(12) United States Patent
Wenke et al.

(10) Patent No.: US 6,379,399 B1
(45) Date of Patent: Apr. 30, 2002

(54) OXIDATION HAIR DYEING SYSTEMS AND PROCESS FOR PROVIDING MORE EQUALIZED COLORATION ON NEW AND OLD GROWTH HAIR

(75) Inventors: Gottfried Wenke, Woodbridge; Michael Y. M. Wong, Easton, both of CT (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/504,818

(22) Filed: Feb. 16, 2000

(51) Int. Cl.$^7$ .................................................. A61K 7/13
(52) U.S. Cl. .................................. 8/409; 8/423; 8/421
(58) Field of Search ........................... 8/405, 406, 407, 8/408, 409, 416, 421, 423, 424

(56) References Cited

U.S. PATENT DOCUMENTS

| | | | |
|---|---|---|---|
| 3,630,655 A | 12/1971 | Berth | 8/11 |
| 3,898,032 A | 8/1975 | Edman et al. | 8/10.2 |
| 5,021,067 A | 6/1991 | Grollier | 8/409 |

FOREIGN PATENT DOCUMENTS

| | | | |
|---|---|---|---|
| DE | 27 14 955 A1 | 10/1978 | A61K/7/13 |
| FR | 1398193 A | 3/1965 | |

OTHER PUBLICATIONS

Venkataraman, The Chemistry of Synthetic Dyes, vol. 5, Academic Press p 294–505, 1971.*

Derwent Abstract of DE–2714955 A, Oct. 1978.*

* cited by examiner

Primary Examiner—Margaret Einsmann
(74) Attorney, Agent, or Firm—Charles J. Zeller

(57) ABSTRACT

Oxidative hair dyeing systems are provided that are "root seeking", i.e., which produce more intense initial coloration on new growth, less porous hair compared to the initial coloration produced in older, damaged, more porous hair. More equalized coloration along the shaft of hair can be obtained with the "root seeking" dyeing products.

32 Claims, No Drawings

OXIDATION HAIR DYEING SYSTEMS AND PROCESS FOR PROVIDING MORE EQUALIZED COLORATION ON NEW AND OLD GROWTH HAIR

FIELD OF THE INVENTION

The invention relates to an oxidative hair dyeing system and process for producing more equalized coloration of hair along the shaft of the hair from new growth hair to old growth hair. More particularly, the invention relates to an oxidative hair dye system employing at least one primary intermediate and at least one coupler which are oxidized to form a coupled dye product in the hair, which coupler dye product is of greater stability to alkaline hydrogen peroxide solution in less porous virgin hair than in more porous damaged hair such that the intensity of the resulting coloration of the hair is more equalized along the shaft of the hair. The invention further relates to an oxidative hair dyeing system in which the initial coloration on new growth hair is more intense than the coloration on old growth or damaged hair.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

However, the condition and structure of human hair is not identical or regular along the entire length of the hair shaft. There is a wide variance of conditions and structure between virgin or new growth hair and older, non-virgin or damaged hair due to a variety of conditions to which human hair is subject. Human hair is subject to a wide variety of conditions, for example, various chemical and mechanical treatments, such as brushing, combing, shampooing, perming, heat treatments, exposure to the sun and the like. The various chemical and mechanical treatments result in the hair becoming progressively more damaged as exposure to these treatments increase. As such, the oldest growth hair at the tips or ends of the hair shaft will generally exhibit greater damage relative to the new growth hair closest to the scalp. The more damaged hair is more porous than the relatively undamaged new growth hair. As a result, inconsistent coloration of the hair is generally obtained in an oxidative dyeing process due to the variable or irregular uptake of the coloring agents along the length of the hair shaft from the virgin hair to the oldest growth hair. Under normal dyeing conditions both oxidative as well as direct dyes color damaged tips of hair shafts to a more intense color than undamaged hair found at the root of the hair shaft.

There is therefore a need for hair coloring systems, compositions and a process which can provide more equalized hair coloration along the length of the shaft of hair, i.e., which can produce substantially more consistent hair coloration along the entire length of a shaft of hair. There is also a need for such systems, compositions and processes which, in addition to providing more equalized hair coloration along the shaft of hair, also provides hair coloration resistant to fading due to washing, shampooing and exposure to the sun.

BRIEF SUMMARY OF THE INVENTION

The invention provides an oxidative dyeing process for producing more equalized coloration of hair along the length of a shaft of the hair, the process comprising:
providing an oxidative hair coloring system comprising an at least one primary intermediate, at least one coupler, and an alkaline hydrogen peroxide or hydrogen peroxide precursor solution;
contacting the hair with the oxidative hair coloring system for an effective period of time to color the hair; and
rinsing, shampooing and drying the hair;
wherein the at least one primary intermediate and the at least one coupler are oxidized to form a coupled dye product in the hair, and the coupled dye product is of greater stability to alkaline hydrogen peroxide solution in less porous virgin hair than in more porous damaged hair such that the intensity of the resulting coloration of the hair is more equalized along the shaft of the hair.

The invention further provides an oxidative hair coloring system for producing more equalized coloration of a shaft of hair along the length of the hair shaft from less porous virgin hair to more porous damaged hair, the hair coloring system comprising:
at least one primary intermediate;
at least one coupler; and
an alkaline solution of hydrogen peroxide or hydrogen peroxide precursor;
the at least one primary intermediate and the at least one coupler being such as to form an oxidatively coupled dye product in the hair stem by the action of hydrogen peroxide from the alkaline solution, and said oxidatively coupled dye product being characterized by greater stability to alkaline hydrogen peroxide solution in the less porous virgin hair than in the more porous damaged hair such that upon dyeing of hair more equalized intensity of coloration is obtainable along the length of the hair shaft.

The invention also provides an oxidative dyeing process for producing coloration of hair along the length of a shaft of the hair, the process comprising:
providing an oxidative hair coloring system comprising an at least one primary intermediate, at least one coupler, and an alkaline hydrogen peroxide or hydrogen peroxide precursor solution;
contacting the hair with the oxidative hair coloring system for an effective period of time to color the hair; and
rinsing, shampooing and drying the hair;
wherein the at least one primary intermediate and the at least one coupler are oxidized to form a coupled dye product in the hair, and the coupled dye product initially produces more intense coloration in less porous virgin hair than in more porous damaged hair.

DETAILED DESCRIPTION OF INVENTION AND PREFERRED EMBODIMENTS

The invention provides an oxidation dyeing process for the coloration of hair in which more equalized intensity of coloration of a shaft of the hair is obtained along a length of the shaft of hair from less porous virgin hair to more porous damaged hair, the process comprising dyeing the hair with a hair coloring system comprising a hydrogen peroxide oxidatively coupled dye product of at least one primary intermediate and at least one coupler, wherein the oxidatively coupled dye product formed in the hair shaft has a high reactivity with alkaline hydrogen peroxide such that increasing amounts of said oxidatively coupled dye product is destroyed within the hair as the porosity of the hair increases from less porous virgin hair to more porous damaged hair whereby the resulting intensity of coloration along the shaft of the hair is brought into closer equalization.

The invention further provides an oxidative hair coloring system for the coloration of hair for producing more equalized intensity of coloration of a shaft of the hair along a length of the shaft of the hair from less porous virgin hair to more porous damaged hair, the hair coloring system comprising:

at least one primary intermediate;

at least one coupler; and an alkaline solution of hydrogen peroxide or hydrogen peroxide precursor;

the at least one primary intermediate and the at least one coupler being such as to form an oxidatively coupled dye product in the hair stem by the action of hydrogen peroxide from the alkaline solution, and said oxidatively coupled dye product being characterized by a high reactivity with alkaline hydrogen peroxide such that increasing amount of said oxidatively coupled dye product is destroyable within the hair as the porosity of the hair increases from less porous virgin hair to more porous damaged hair whereby the hair coloring system can bring the intensity of coloration along the shaft of the hair into closer equalization.

In another aspect, the invention provides an oxidative hair coloring system for the coloration of hair for producing coloration of a shaft of the hair along a length of the shaft of the hair from less porous virgin hair to more porous damaged hair, the hair coloring system comprising:

at least one primary intermediate;

at least one coupler; and an alkaline solution of hydrogen peroxide or hydrogen peroxide precursor;

the at least one primary intermediate and the at least one coupler being such as to form an oxidatively coupled dye product in the hair stem by the action of hydrogen peroxide from the alkaline solution, and said oxidatively coupled dye product being characterized by a high reactivity with alkaline hydrogen peroxide such that said oxidatively coupled dye initially produces a more intense coloration in less porous virgin hair than the initial coloration produced in more porous damaged hair.

It is believed that more equalized coloration of hair along the shaft of the hair is obtained in accordance with this invention by providing a coupled dye product in the hair shaft that is more readily destroyed by hydrogen peroxide in the more porous, damaged, older hair than it is in the less porous new hair. With the process and hair coloring system of this invention, a stronger, more intense initial coloration is produced on intact new hair than the initial coloration provided on damaged hair by the provision of a coupled dye product in the hair shaft that has a higher reactivity with alkaline hydrogen peroxide or hydrogen peroxide precursor whereby more coupled dye product (color) is destroyed in porous damaged hair than in initial new or virgin hair so that more equalized coloration of the hair results along the shaft of the hair. Thus, the coupled dye product of this invention is regarded as a "root-seeking" dye.

In accordance with this invention, oxidative hair dyeing systems, compositions and processes are provided in which the coupler employed is 2-amino-8-hydroxyquinoline. This coupler is employed with one or more suitable primary intermediates that form a root-seeking coupled dye product with the 2-amino-8-hydroxyquinoline to produce a stronger, more intense coloration on new or virgin hair than on older, more porous damaged hair.

As suitable primary intermediates that form such coupled dye product with 2-amino-8-hydroxyquinoline to produce more intense coloration on new hair compared to older damaged hair, there may be mentioned N,N-bis (hydroxyethyl)-p-phenylenediamine and 2-aminophenol. The fact that new hair is more intensely colored than older damaged hair is surprising in itself and is rendered even more surprising by the fact that such a result is not obtained with coupled dye products obtained with closely related 8-hydroxyquinoline compounds.

The hair coloring systems and compositions of this invention will contain the coupler of this invention, alone or in combination with other couplers, in an effective coloring amount, generally in an amount of from about 0.01 to about 2.5 weight percent. The primary intermediate(s) will generally be present in an amount of from about 0.01 to about 3.5 weight percent. The molar ratio of primary intermediate to coupler will generally range from about 5:1 to about 1:5, preferably at an equimolar (1:1) ratio, and be employed in any suitable carrier or vehicle, generally an aqueous or hydroalcoholic solution, preferably an aqueous solution. The carrier or vehicle will generally comprise up to about 40 weight percent.

The hair coloring compositions of this invention may contain one or more cationic, anionic or amphoteric surface active agents, perfumes, antioxidants, sequestering agents, thickening agents, alkalizing or acidifying agents, and other dyeing agents.

Any suitable peroxide providing agent can be employed in the coloring compositions of this invention, particularly hydrogen peroxide ($H_2O_2$) or precursors therefor.

The invention is illustrated but not limited by the following examples.

EXAMPLES 1 TO 3

The selectivity of the coupled dye products of this invention for intact, new, less porous hair compared to older, damaged, more porous hair is demonstrated by the tests conducted in the following examples, namely Example 1 of this invention and Comparative Examples 2 and 3. The tests were conducted by dyeing untreated Piedmont hair (representing new, less porous hair) and bleached Piedmont hair (representing damaged, more porous hair) in the same dye bath under identical dyeing conditions. The dyeing of the untreated and bleached Piedmont hair was conducted by dyeing the hair in a dye base mixed 1:1, by weight, with 10 Vol. $H_2O_2$ at a dyeing time of 30 minutes, after which the hair is rinsed, shampooed and dried. In the examples, dyeing was conducted with a dyeing solution of an 8-hydroxyquinoline coupler and N,N-bis(hydroxyethyl)-p-phenylenediamine and 10 volumes $H_2O_2$. In Example 1, the coupler was 2-amino-8-hydroxyquinoline, in Comparative Example 2 the coupler was 5-amino-8-hydroxyquinoline and in Comparative Example 3 the coupler was 7-propyl-8-hydroxyquinoline. The dye concentration was 2.86 mmole/100 g (before mixing with $H_2O_2$).

After dyeing, the color difference between the undyed and dyed hair for both the untreated and bleached Piedmont hair was measured using a Minolta spectrophotometer Chroma Meter 3700d reflectometer. The Minolta Chroma Meter 3700d spectrophotometer uses reflected light from a surface and gives results in terms of the CIE (International Commission on Illumination) tristimulus values. These values are subsequently transformed mathematically into the L* a* b* color space, wherein the magnitude of changes in hue and intensity of color correspond closely with those perceived by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y-axis to give quantitative color information: "metric chroma" is the length of a line from the origin (a*=0, b*=0) to the point of a sample reading while metric hue angle is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

A measure of the color intensity on the hair is $\Delta C$ which is defined as $\sqrt{(\Delta L^{*2})+(\Delta a^{*2})+(\Delta b^{*2})}$.

The results of the tests are set forth in the following Table. The baseline average values of L*, a* and b* for undyed, untreated Piedmont hair were L* 72.32, a* 2.0, b* 23.2 and for undyed, bleached Piedmont hair were L* 78.1, a* −1.5, b* 18.9.

TABLE

| Example | Hair | CIE Color Space L* a* b* | | | ΔC |
|---|---|---|---|---|---|
| 1a | Piedmont | 34.2 | −10.1 | −6.3 | 49.3 |
| 1b | Bleached Piedmont | 37.5 | −7.5 | −0.6 | 45.7 |
| 2a | Piedmont | 51.1 | −0.2 | 14.8 | 22.9 |
| 2b | Bleached Piedmont | 48.6 | −1.4 | 12.0 | 30.3 |
| 3a | Piedmont | 39.5 | −11.4 | −8.8 | 47.4 |
| 3b | Bleached Piedmont | 37.6 | −10.9 | −9.6 | 50.9 |

The results demonstrate that 2-amino-8-hydroxyquinoline provides more intense coloration to untreated Piedmont hair (Example 1a) than to treated Piedmont hair (Example 1b), i.e., has better selectivity for intact less porous hair than for damaged more porous hair. In contrast, neither 5-amino-8-hydroxyquinoline nor 7-propyl-8-hydroxyquinoline show such a preference for intact less porous hair.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. An oxidative dyeing process for producing coloration of hair along the length of a shaft of the hair, the process comprising:
    providing an oxidative hair coloring system comprising at least one primary intermediate, at least one coupler comprising 2-amino-8-hydroxyquinoline, and an alkaline hydrogen peroxide or hydrogen peroxide precursor solution;
    contacting the hair with the oxidative hair coloring system for an effective period of time to color the hair; and
    rinsing, shampooing and drying the hair;
    wherein the at least one primary intermediate and the at least one coupler are oxidized to form a coupled dye product in the hair, and the coupled dye product is of greater stability to alkaline hydrogen peroxide solution in less porous virgin hair than in more porous damaged hair.

2. A process according to claim 1 wherein the at least one primary intermediate is selected from N,N-bis (hydroxyethyl)-p-phenylenediamine and o-aminophenol.

3. A process according to claim 2 wherein the at least one primary intermediate comprises N,N-bis(hydroxyethyl)-p-phenylenediamine.

4. A process according to claim 2 wherein the at least one primary intermediate comprises o-aminophenol.

5. An oxidation dyeing process for the coloration of hair along a length of the shaft of hair from less porous virgin hair to more porous damaged hair, the process comprising dyeing the hair with a hair coloring system comprising a hydrogen peroxide oxidatively coupled dye product of at least one primary intermediate and at least one coupler comprising 2-amino-8-hydroxyquinoline, wherein the oxidatively coupled dye product formed in the hair shaft has a high reactivity with alkaline hydrogen peroxide such that increasing amounts of said oxidatively coupled dye product is destroyed within the hair as the porosity of the hair increases from less porous virgin hair to more porous damaged hair.

6. A process according to claim 5 wherein the at least one primary intermediate is selected from N,N-bis (hydroxyethyl)-p-phenylenediamine and o-aminophenol.

7. A process according to claim 6 wherein the at least one primary intermediate comprises N,N-bis(hydroxyethyl)-p-phenylenediamine.

8. A process according to claim 6 wherein the at least one primary intermediate comprises o-aminophenol.

9. An oxidative hair coloring system for producing coloration of a shaft of hair along the length of the hair shaft from less porous virgin hair to more porous damaged hair, the hair coloring system comprising:
    at least one primary intermediate;
    at least one coupler comprising 2-amino-8-hydroxyquinoline; and
    an alkaline solution of hydrogen peroxide or hydrogen peroxide precursor;
    the at least one primary intermediate and the at least one coupler being such as to form an oxidatively coupled dye product in the hair shaft by the action of hydrogen peroxide from the alkaline solution, and said oxidatively coupled dye product being characterized by greater stability to alkaline hydrogen peroxide solution in the less porous virgin hair than in the more porous damaged hair.

10. A system according to claim 9 wherein the at least one primary intermediate is selected from N,N-bis (hydroxyethyl)-p-phenylenediamine, o-aminophenol and mixtures thereof.

11. A system according to claim 10 wherein the at least one primary intermediate comprises N,N-bis(hydroxyethyl)-p-phenylenediamine and o-aminophenol.

12. A system according to claim 10 wherein the at least one primary intermediate comprises o-aminophenol.

13. An oxidative hair coloring system for the coloration of hair for producing essentially equalized intensity of coloration of a shaft of the hair along a length of the shaft of the hair from less porous virgin hair to more porous damaged hair, the hair coloring system comprising:

at least one primary intermediate;

at least one coupler comprising 2-amino-8-hydroxyquinoline; and an alkaline solution of hydrogen peroxide or hydrogen peroxide precursor;

the at least one primary intermediate and the at least one coupler being such as to form an oxidatively coupled dye product in the hair shaft by the action of hydrogen peroxide from the alkaline solution, and said oxidatively coupled dye product being characterized by a high reactivity with alkaline hydrogen peroxide such that increasing amount of said oxidatively coupled dye product is destroyable within the hair as the porosity of the hair increases from less porous virgin hair to more porous damaged hair.

14. A system according to claim 13 wherein the at least one primary intermediate is selected from N,N-bis(hydroxyethyl)-p-phenylenediamine, and o-aminophenol and mixtures thereof.

15. A system according to claim 14 wherein the at least one primary intermediate comprises N,N-bis(hydroxyethyl)-p-phenylenediamine and o-aminophenol.

16. A system according to claim 14 wherein the at least one primary intermediate comprises o-aminophenol.

17. An oxidative dyeing process for producing coloration of hair along the length of a shaft of the hair, the process comprising:

providing an oxidative hair coloring system comprising an at least one primary intermediate, at least one coupler comprising 2-amino-8-hydroxyquinoline, and an alkaline hydrogen peroxide or hydrogen peroxide precursor solution;

contacting the hair with the oxidative hair coloring system for an effective period of time to color the hair; and rinsing, shampooing and drying the hair;

wherein the at least one primary intermediate and the at least one coupler are oxidized to form a coupled dye product in the hair, and the coupled dye product initially produces more intense coloration in less porous virgin hair than in more porous damaged hair.

18. A process according to claim 17 wherein the at least one primary intermediate is selected from N,N-bis(hydroxyethyl)-p-phenylenediamine and o-aminophenol.

19. A process according to claim 18 wherein the at least one primary intermediate comprises N,N-bis(hydroxyethyl)-p-phenylenediamine.

20. A process according to claim 18 wherein the at least one primary intermediate comprises o-aminophenol.

21. An oxidative hair coloring system for the coloration of hair for producing coloration of a shaft of the hair along a length of the shaft of the hair from less porous virgin hair to more porous damaged hair, the hair coloring system comprising:

at least one primary intermediate;

at least one coupler comprising 2-amino-8-hydroxyquinoline; and an alkaline solution of hydrogen peroxide or hydrogen peroxide precursor;

the at least one primary intermediate and the at least one coupler being such as to form an oxidatively coupled dye product in the hair shaft by the action of hydrogen peroxide from the alkaline solution, and said oxidatively coupled dye product being characterized by a high reactivity with alkaline hydrogen peroxide such that said oxidatively coupled dye initially produces a more intense coloration in less porous virgin hair than the initial coloration produced in more porous damaged hair.

22. A system according to claim 21 wherein the at least one primary intermediate is selected from N,N-bis(hydroxyethyl)-p-phenylenediamine, o-aminophenol and mixtures thereof.

23. A system according to claim 22 wherein the at least one primary intermediate comprises N,N-bis(hydroxyethyl)-p-phenylenediamine and o-aminophenol.

24. A system according to claim 22 wherein the at least one primary intermediate comprises o-aminophenol.

25. A hair coloring composition for dyeing human hair comprising, in a suitable carrier or vehicle, a dyeing effective amount of:

(a) at least one primary intermediate, (b) at least one coupler comprising 2-amino-8-hydroxyquinoline, and (c) a hydrogen peroxide or hydrogen peroxide precursor.

26. A hair coloring composition according to claim 25 wherein the at least one primary intermediate is selected from N,N-bis(hydroxyethyl)-p-phenylenediamine.

27. A hair coloring composition according to claim 26 wherein the at least one primary intermediate comprises N,N-bis(hydroxyethyl)-p-phenylenediamine and o-aminophenol.

28. A hair coloring composition according to claim 26 wherein the at least one primary intermediate comprises o-aminophenol.

29. A process for dyeing human hair comprising applying a dyeing effective amount of a hair coloring composition of claim 25 to the hair and permitting the composition to contact the hair for a dyeing effective period of time, and the rinsing, shampooing and drying the hair.

30. A process for dyeing human hair comprising applying a dyeing effective amount of a hair coloring composition of claim 26 to the hair and permitting the composition to contact the hair for a dyeing effective period of time, and the rinsing, shampooing and drying the hair.

31. A process for dyeing human hair comprising applying a dyeing effective amount of a hair coloring composition of claim 27 to the hair and permitting the composition to contact the hair for a dyeing effective period of time, and the rinsing, shampooing and drying the hair.

32. A process for dyeing human hair comprising applying a dyeing effective amount of a hair coloring composition of claim 28 to the hair and permitting the composition to contact the hair for a dyeing effective period of time, and the rinsing, shampooing and drying the hair.

* * * * *